(12) United States Patent
Campbell et al.

(10) Patent No.: US 11,604,138 B2
(45) Date of Patent: Mar. 14, 2023

(54) MINIMIZATION OF NOISE IN OPTICAL DATA CAPTURE FOR LIQUIDS

(71) Applicant: Liquid Sensing, Inc, Newbury Park, CA (US)

(72) Inventors: Thomas Campbell, Newbury Park, CA (US); Jacob Y Wong, Goleta, CA (US)

(*) Notice: Subject to any disclaimer, the term of this patent is extended or adjusted under 35 U.S.C. 154(b) by 53 days.

(21) Appl. No.: 17/227,789

(22) Filed: Apr. 12, 2021

(65) Prior Publication Data

US 2021/0231559 A1    Jul. 29, 2021

Related U.S. Application Data

(63) Continuation of application No. 17/073,297, filed on Oct. 17, 2020, now Pat. No. 10,976,243, which is a continuation-in-part of application No. 16/600,466, filed on Oct. 12, 2019, now Pat. No. 10,983,046, which is a continuation-in-part of application No.
(Continued)

(51) Int. Cl.
*A61B 5/1455* (2006.01)
*A61B 5/145* (2006.01)
*A61B 5/00* (2006.01)
*G01N 21/31* (2006.01)
*G01N 33/487* (2006.01)
*G01N 21/35* (2014.01)
*G01N 21/3577* (2014.01)
*G01N 21/21* (2006.01)
*G01N 33/49* (2006.01)

(52) U.S. Cl.
CPC ....... *G01N 21/3151* (2013.01); *A61B 5/0075* (2013.01); *A61B 5/1451* (2013.01); *A61B 5/1455* (2013.01); *A61B 5/14532* (2013.01); *G01N 21/3577* (2013.01); *G01N 33/487* (2013.01); *A61B 5/0062* (2013.01); *A61B 2562/0238* (2013.01); *G01N 21/21* (2013.01); *G01N 33/49* (2013.01); *G01N 2021/3148* (2013.01); *G01N 2201/10* (2013.01)

(58) Field of Classification Search
CPC ... A61B 5/0062; A61B 5/0075; A61B 5/1451; A61B 5/14532; A61B 5/1455; A61B 2562/0238; G01N 21/21; G01N 21/3151; G01N 21/3577; G01N 33/487; G01N 33/49; G01N 2021/3148; G01N 2201/10
See application file for complete search history.

(56) References Cited

U.S. PATENT DOCUMENTS 6,509,567 B2 * 1/2003 Boudet ................ G01N 21/314
250/575

* cited by examiner

*Primary Examiner* — Mark R Gaworecki
(74) *Attorney, Agent, or Firm* — Roy L Anderson

(57) ABSTRACT

A process quantifies a concentration of a targeted molecule in a liquid sample by pulsing signal and reference beams from their own sources, then spatially combining the pulsed beams into a single radiation beam which passes into the liquid sample and then detecting pulsed output beams after the single radiation beam passes out of the liquid sample. The pulsed outputs of the signal and reference beams are processed to obtain a value over a preselected period of time and, if an interference beam is used, it is processed with the reference beam to obtain a calibration curve adjustment representative of optical interference represented by at least one interfering molecule concentration which is used to calculate the concentration level of the targeted particle in the liquid sample. Two detectors, which may have an optical co-axial configuration, can be used for detection of pulsed beams.

17 Claims, 20 Drawing Sheets

Related U.S. Application Data

16/359,350, filed on Mar. 20, 2019, now Pat. No. 10,473,586, which is a continuation-in-part of application No. 16/056,531, filed on Aug. 7, 2018, now Pat. No. 10,241,044, which is a continuation-in-part of application No. 15/785,829, filed on Oct. 17, 2017, now Pat. No. 10,041,881, which is a continuation-in-part of application No. 15/644,775, filed on Jul. 8, 2017, now Pat. No. 9,823,185, which is a continuation-in-part of application No. 15/594,418, filed on May 12, 2017, now Pat. No. 9,726,601, which is a continuation-in-part of application No. 15/444,136, filed on Feb. 27, 2017, now Pat. No. 9,678,000, which is a continuation-in-part of application No. 15/358,873, filed on Nov. 22, 2016, now Pat. No. 9,606,053.

MINIMIZATION OF NOISE IN OPTICAL DATA CAPTURE FOR LIQUIDS

CROSS-REFERENCE TO RELATED APPLICATIONS

The present invention is a continuation application of U.S. Ser. No. 17/073,297, filed Oct. 17, 2020, which was a continuation-in-part application of U.S. Ser. No. 16/600, 466, filed Oct. 12, 2019, which is a continuation of U.S. Ser. No. 16/359,350, filed Mar. 20, 2019, which was a continuation-in-part application of U.S. Ser. No. 16/056,531, filed Aug. 7, 2018, which is a continuation-in-part of U.S. Ser. No. 15/785,829 filed Oct. 17, 2017, which is a continuation-in-part of U.S. Ser. No. 15/644,775 filed Jul. 8, 2017, which is a continuation in part of U.S. Ser. No. 15/594,418 filed May 12, 2017, which is a continuation-in-part application of U.S. Ser. No. 15/444,136 filed Feb. 27, 2017, which is a continuation-in-part application of U.S. Ser. No. 15/358,873, filed Nov. 22, 2016, the disclosures of all of which are specifically incorporated herein by reference.

FIELD OF THE INVENTION

The present invention relates to an improved absorption method to detect molecules in the liquid phase.

BACKGROUND OF THE INVENTION

Non-Dispersive Infra-Red (NDIR) is a common and excellent measurement technique for detecting gases in the atmosphere. NDIR sensors utilize the principle that various gas molecules exhibit substantial absorption at specific wavelengths in the infrared radiation spectrum. The term "non-dispersive" as used herein refers to the apparatus used, typically a narrow-band optical or infrared transmission filter, instead of a dispersive element such as a prism or diffraction grating. The optical filter isolates the radiation in a particular wavelength band that coincides with a strong absorption band of a gas species for the purpose of said gas species measurement.

The present invention builds upon past inventions disclosed in related applications to further advance use of NDIR to detect molecules in a liquid medium.

This and further objects and advantages will be apparent to those skilled in the art in connection with the figures and the detailed description of the invention set forth below.

SUMMARY OF THE INVENTION

The present invention is generally directed to a process for quantifying a concentration of a targeted molecule in a liquid sample in which a signal beam and a reference beam (and also optionally an interference beam) are pulsed, each beam being pulsed from its own source (preferably at narrow bandwidths), the pulsed beams are spatially combined into a single radiation beam which passes into the liquid sample and then pulsed output beams are detected after the single radiation beam passes out of the liquid sample. The pulsed signal beam output and the pulsed reference beam are processed to obtain a value over a preselected period of time and, if an interference beam is used, it is processed with the reference beam to obtain a calibration curve adjustment representative of optical interference represented by at least one interfering molecule concentration which is used to calculate the concentration level of the targeted particle in the liquid sample. Two detectors, which may have an optical co-axial configuration, can be used for detection of pulsed beams.

The object of the present invention is to provide an improved system and process for detection of molecules in a liquid medium.

This and further objects and advantages will be apparent to those skilled in the art in connection with the figures and the detailed description of the invention set forth below.

DETAILED DESCRIPTION OF THE INVENTION

Figure 1:
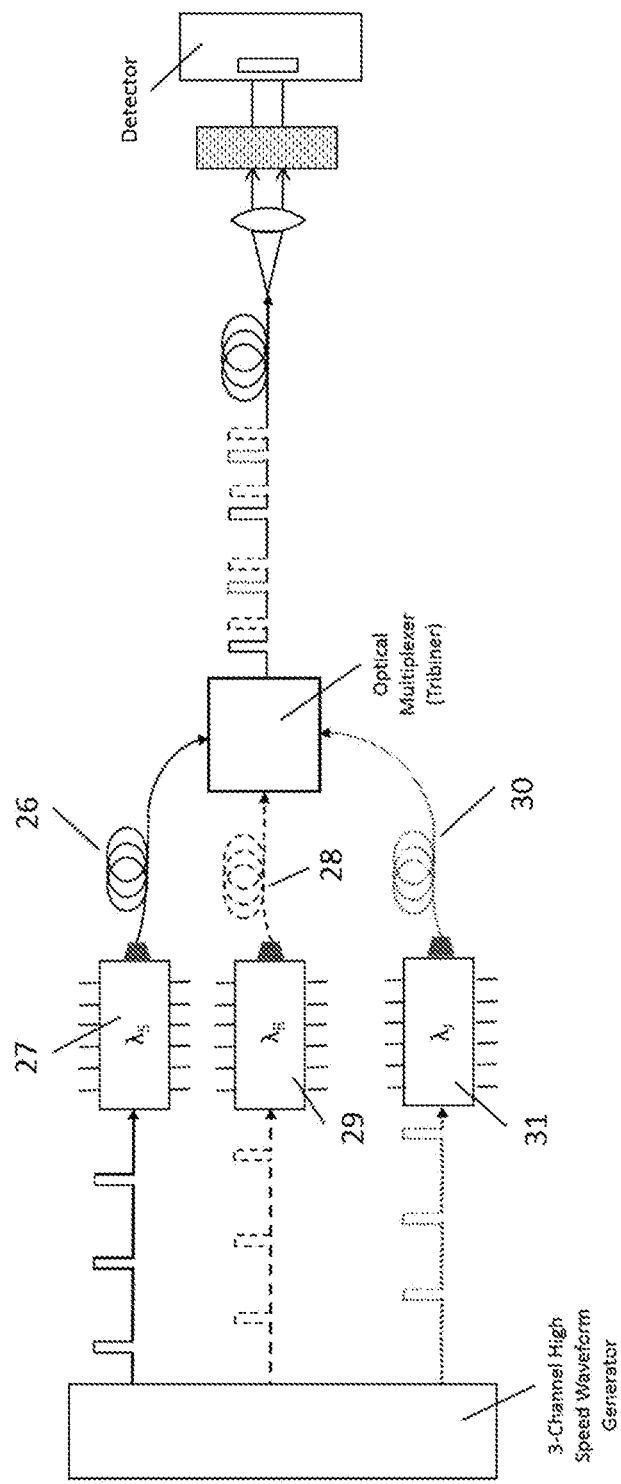
FIG. 1 illustrates an optical setup illustrating how a Signal diode laser, a Reference diode laser and an Interference diode laser are driven alternatively and successively by a 3-channel high speed waveform generator.

U.S. Pat. No. 9,606,053 (2017) discloses an NDIR method which significantly suppresses scattering noise attributable to the much higher molecular density which is encountered in a liquid medium, as opposed to a gaseous medium. The method utilizes alternating and successively pulsing infrared radiation from signal and reference sources which are multiplexed and collimated into a single pulsed beam directed through the liquid sample. The pulse frequency is set sufficiently fast so as to provide almost the same molecular configuration to both the signal and the reference beams. The scattering noise encountered by both beams is effectively the same and can be significantly reduced through processing the ratio of their respective pass-through outputs.

U.S. Pat. No. 9,678,000 (2017) discloses using an NDIR method to detect glucose in a liquid medium. Glucose has an overtone absorption band located at 1,150 nm which can be used as the center wavelength for the signal beam. This absorption band is desirable because it has a water absorption coefficient of no greater than ~1.0 cm$^{-1}$, which is especially preferred, as it helps to minimize effects created by water absorption. A reference beam wavelength of 1,064 nm, where there is no glucose molecule absorption, can be used as the center wavelength for the reference beam.

U.S. Pat. No. 9,726,601 (2017) discloses an improved NDIR method for determining the concentration of targeted molecules labeled M in a liquid medium admixed with interfering molecules labeled $M_J$ which uses an additional interference radiation source besides those of the signal and reference to significantly reduce the interference noise. U.S. Pat. No. 9,823,185 (2017) discloses an improvement to this method with suppression of both scattering and absorption interference noise (AIN) via a reflection detection technique.

U.S. Pat. No. 10,475,586 discloses a signal source, an interference source, a reference source, a multiplexer and a collimator to pulse radiation in a pulsed beam which is detected by a detector as is described in greater detail in U.S. Pat. Nos. 9,606,053 and 9,823,185. The signal source emits radiation at a signal wavelength which is within a first absorption band of the targeted molecule M, the interference source emits radiation at an interference wavelength which is within a second absorption band of said at least one interfering molecule $M_J$, and the reference beam emits radiation at a reference wavelength which is neutral and is not within either the first absorption band or the second absorption band; at least one interfering molecule $M_J$ absorbs radiation at the signal wavelength; and the signal source, the interference source and the reference source are each pulsed at a preselected frequency of at least N Hz which is sufficiently fast so that a given molecule of the targeted molecule M or said at least one interfering molecule $M_J$ will not pass in and out of the liquid sampling matrix within the preselected frequency.

Figure 8:
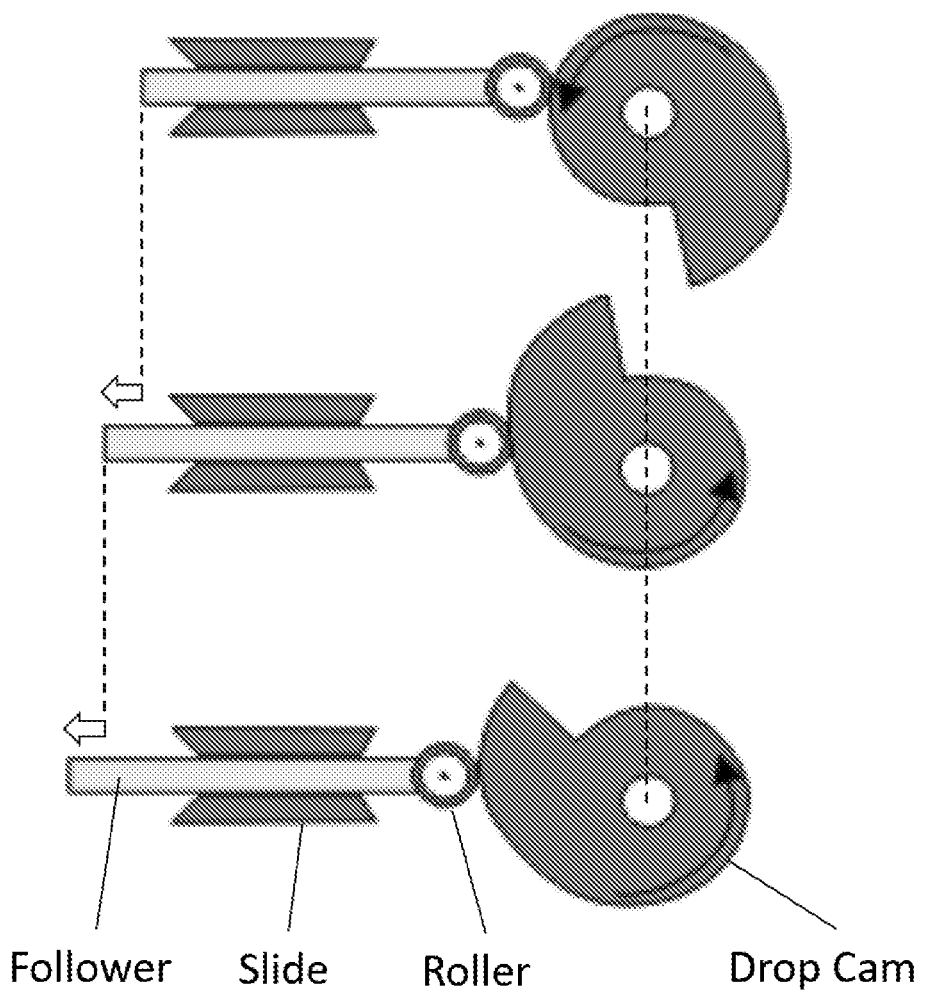

FIG. 1 (which is FIG. 8 in U.S. Pat. No. 9,823,185) illustrates an optical setup of a Signal diode laser, a Reference diode laser and an Interference diode laser which are driven alternately and successively in groups of two by a 3-channel high speed waveform generator. As shown in FIG. 1, output 26 of Signal diode laser 27 is driven alternately and successively with output 28 of Reference diode laser 29 as a pair; meanwhile output 30 of Interference diode laser 31 is driven alternately and successively with output 28 of Reference diode laser 29 as another pair. The rest of the optical and electronic processing system setup for a three-diode laser system to suppress both scattering noise and AIN is the same as the two-diode laser system disclosed in U.S. Pat. No. 9,606,053 (2017) for suppressing just the scattering noise.

U.S. Pat. No. 10,041,881 (2018) discloses an improved NDIR method for liquids in which scattering noise is reduced and an Absorption Interference Noise (AIN) is suppressed with a reflection technique.

U.S. Ser. No. 16/056,531 discloses a process for deciding the validity of the calibration curve for targeted molecules $M_G$ in a liquid sample with interfering molecules. This value can further be used to adjust the calibration curve via a parameter linking the transmittances measured at the signal and interference wavelength channels in order to assure its validity.

A potential limitation of the techniques described in our earlier patents for optical sensing in liquids is a very small sample volume per measurement. In order to enhance the accuracy, precision and reliability of measurements with our inventive Direct Infrared Laser Absorptive Scattering Technique (DILAST) sensors, U.S. Pat. No. 10,473,586 discloses different sample capture techniques.

DILAST optical sensing for liquids can be applied to containerized samples, fluid flows, semi-solid materials, and solid materials all of which have optical permeability such that optical wavelengths can penetrate to some level that allows absorption of target elements or compounds so that detector measurements can be made of said absorption.

For the embodiment of sensing in human tissue, which for the purpose of the present invention will be defined as being a liquid medium which has a dynamic volume with considerable molecular motion incorporating a non-homogenous structure. Many elements and compounds comprise skin with arrangements according to their functions. Knowing that DILAST sensor systems have to work with these complex samples, our prior inventions set forth several methods for improving optical sensor data capture from such samples.

Of the various elements affecting optical absorption in skin, water is the primary absorber by volume. Accounting for hydration of the skin is necessary for highest detection accuracy of glucose in interstitial fluid. Next are various lipids including adipose tissue in skin, followed by melanin in the epidermis, then white blood cells and red blood cells (oxygenated and de-oxygenated) in arteries, veins, and capillaries. Lastly, we step down in volume to proteins, and glucose.

Figure 6:
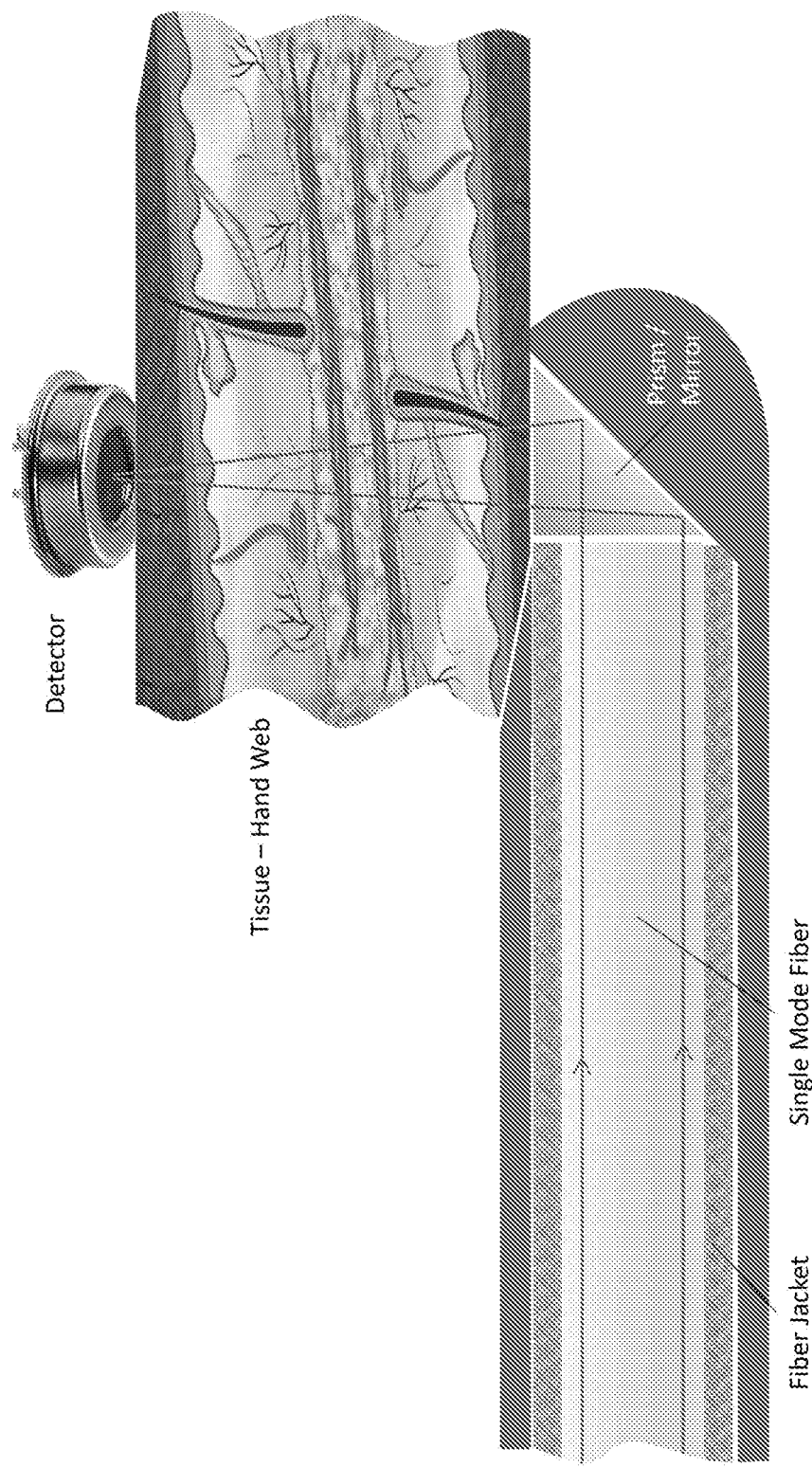
FIG. 6 illustrates a pulsed beam according to the present invention being delivered by way of a single mode optical fiber to a prism or mirror such that the profile is kept low and the controlled light beam can enter the specimen or media under test and transverse the specimen or media in the direction of a detector system that can capture the exiting light energy.

Minimization of the total optical energy imposed on skin is important to the functioning of the DILAST technique. Very specific reference and target species wavelengths are employed to accomplish scattering noise cancellation. And beyond the controlled wavelengths, prior inventions employed a "relatively" small "beam" of optical energy whose resulting scattering and absorption effects are captured on "relatively" small detectors as shown in one configuration described by FIG. 6.

As data manipulation techniques improve with time, one may be able to employ larger beams and be able to process out the larger noise factors. With larger beams, one naturally captures a large sample volume which promotes the goal of high accuracy, precision, and reliability of measurements. However, if one is using a "relatively" small beam, one needs to, in some fashion, scan this beam across a "sample" such that one truly captures a representative data set of the non-homogenous "sample,' and such scanning can be linear, circular, or some combination or hybrid motion such that during the set measurement time, a "comprehensive" data set is captured for calculating values and averaging those values across said "comprehensive" data set. If the samples obtained are not of constant volume, it is especially preferred that non-constant volume illumination must be addressed in the analysis of the data captured to correct for the effects of either larger or smaller "illumination volumes".

Mechanics of the scanning motion according to a prior invention can be implemented with a linear, circular, or combination of linear and circular that best includes a suitable sample volume and subsequent suitable data set, and methods for linear, circular, or hybrid travel can be implemented with electronic, magnetic, or pressure forces. The goal with implementation is smallest size and cost to accomplish the necessary range of motion for a suitable set of scan sites.

Figure 7:
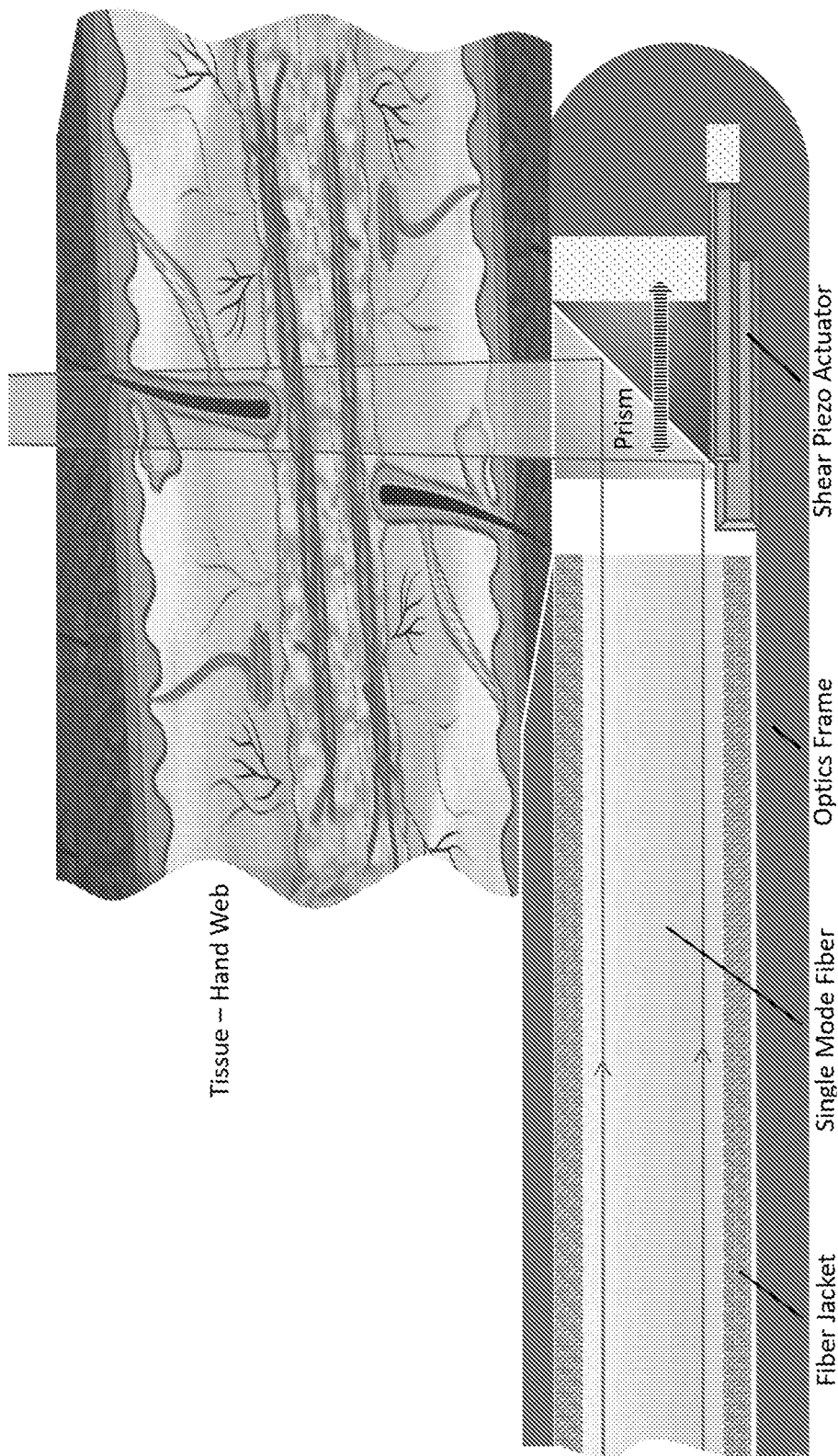
FIG. 7 illustrates the concept of using rotational motion to create a linear scan path by implementation of a rotary drop cam system illustrated in FIG. 8.

One preferred embodiment for implementing scanning motion is to employ a piezo linear or rotary motor which offers high precision and repeatable positioning. There are many other motor elements that can be employed as well. FIG. 7 represents one implementation of a linear motor moving a mirror in a back and forth motion to obtain a linear scan pattern such that the scan sites are identical in volume. FIG. 8 represents the implementation of a rotary motion source to create a linear motion that likewise can move a mirror for stepping a beam across more than one scan sites.

The next step is choosing whether to apply the motion to just the emitter and/or emitter beam and scan across the detector or move the emitter and detector in tandem. The first requires that the detector area is suitable large as to capture data as the emitter and/or emitter beam travels. The second option allows the detector area to remain small and cost-effective, but implementing the tandem travel of the emitter and the detector is more complex.

One embodiment of scanning can be accomplished with a small linear actuator moving a mirror element such that the emitter beam is scanned across multiple sample sites on the test sample or specimen.

Figure 9:
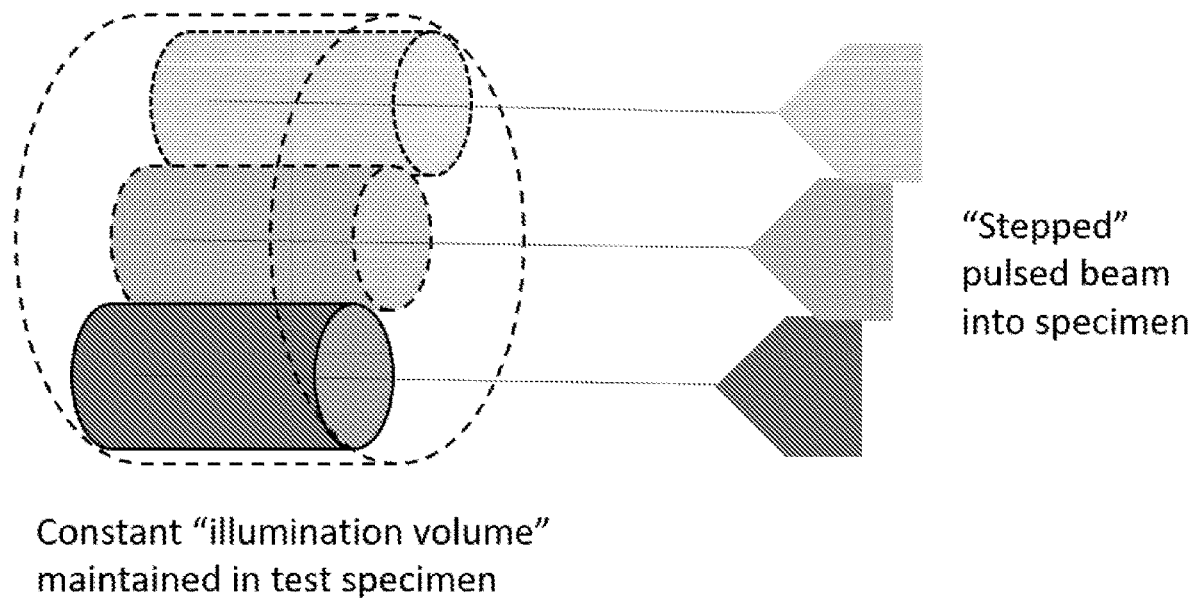
FIG. 9 Illustrates multiple scan sites with a linear scan pattern where each separate scan site comprises a constant volume for equivalent and optimum data capture and comparison analysis.

A shear piezo actuator can linearly move a prism and beam across a scan zone. This scan zone portrayed in FIG. 9 is limited to the available detector area. Multiple sample sites are illuminated for some typical dwell time at each of the three sites in or on the tissue. As noted, the detector area must be sufficiently large to capture reflected and transmitted optical signals. With this technique, a more comprehensive sample is obtained of the tissue that includes interstitial fluid, tissue types, veins, capillaries, follicles, nerves, etc.

Figure 10:
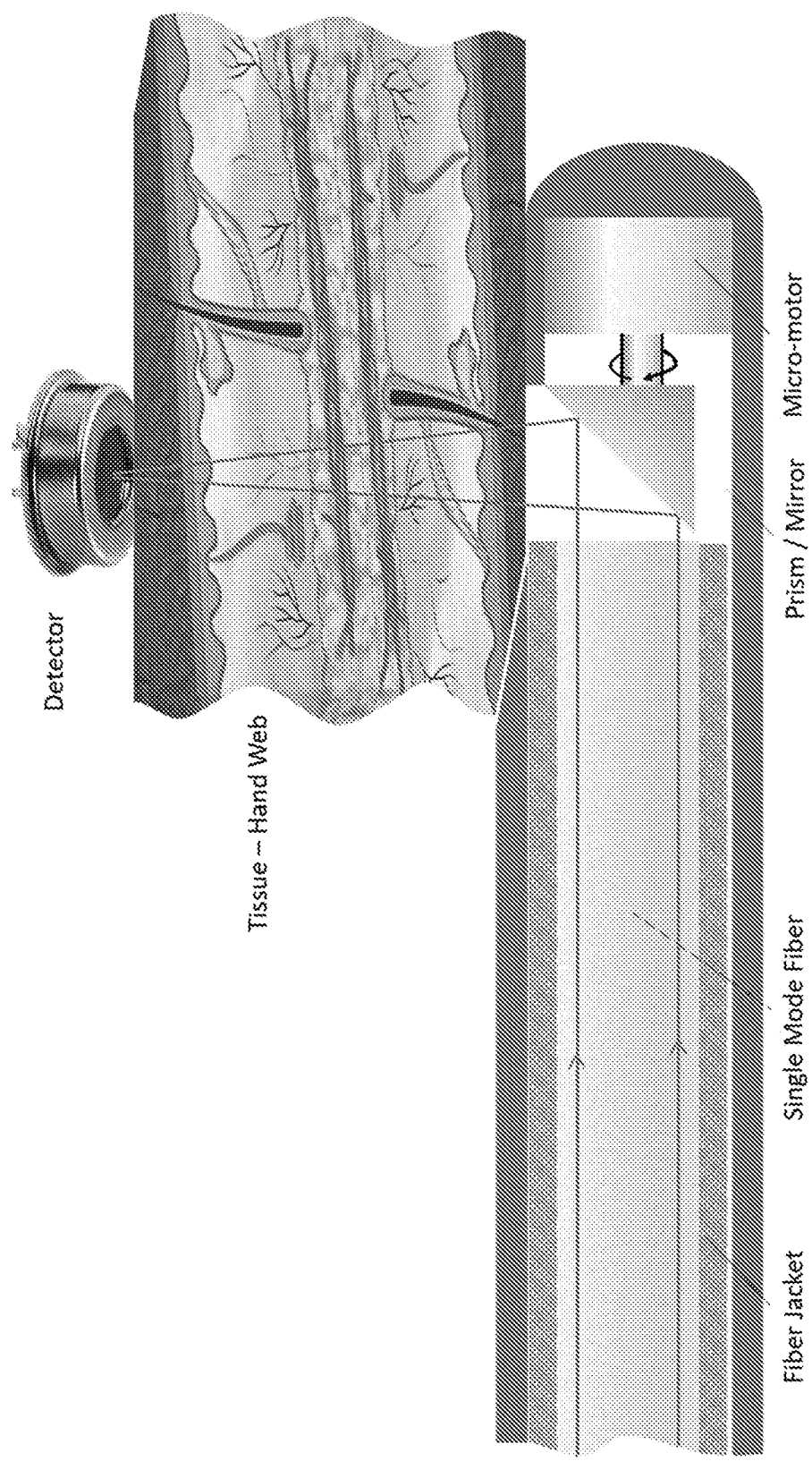
FIG. 10 illustrates one possible method of using rotational motion to establish a scan range of the specimen or media under test by use of a rotating actuator a mirror or some element to redirect the pulsed beam in a precise and consistent fashion.

Another embodiment shown in FIG. 10 uses a rotary element to step the mirror element such that the single beam is directed onto the detector through separate pathways through the sample.

With a goal of ideal optical data capture from skin, one embodiment incorporates three or more illumination locations in the skin by simply moving the light beam and not the detector. The optics to move the light beam are smaller and more precise than moving the detector housing. The detector will require a sufficient surface area to receive energy from each of the scan sites. The use of a mirror should retain properties of the light beam better than a lens system. The actuator choice for moving the mirror should be precise, repeatable, small, and low power.

Figure 11:
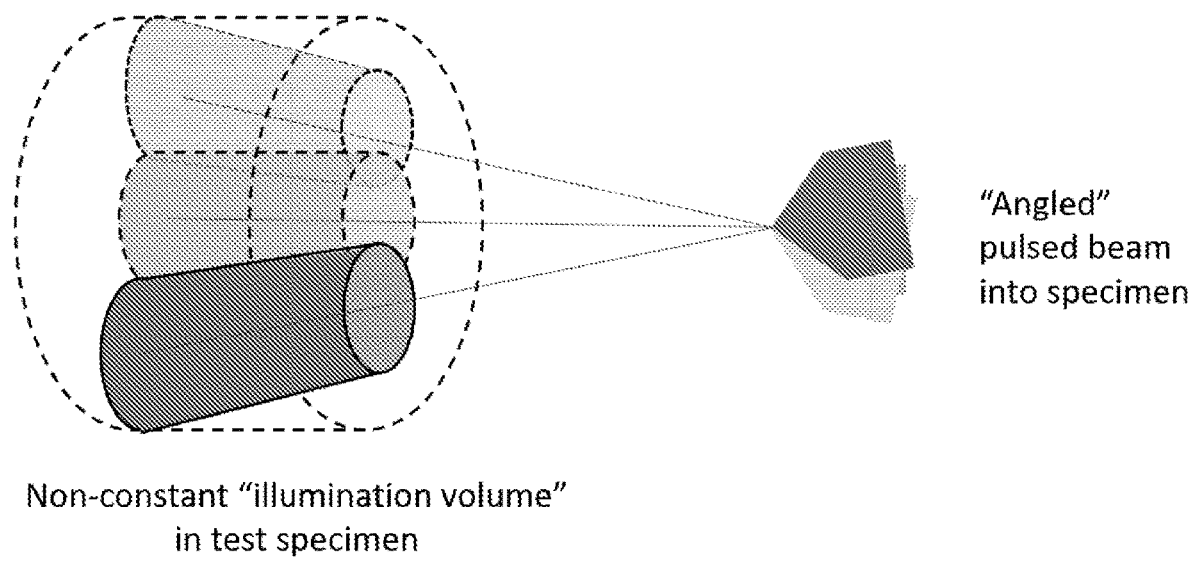
FIG. 11 demonstrates that adding any angularity to the progressive scanning method creates slightly different volumes illuminated in the specimen or media under test.

The scan zone portrayed in FIG. 11 is likewise limited to the available detector area, however, the scan volumes resulting from the angled beams are slightly different. Therefore, the "detected" results must be interpreted to allow for the slightly different reflection, absorption, transmission, and scattering results captured.

Figure 12:
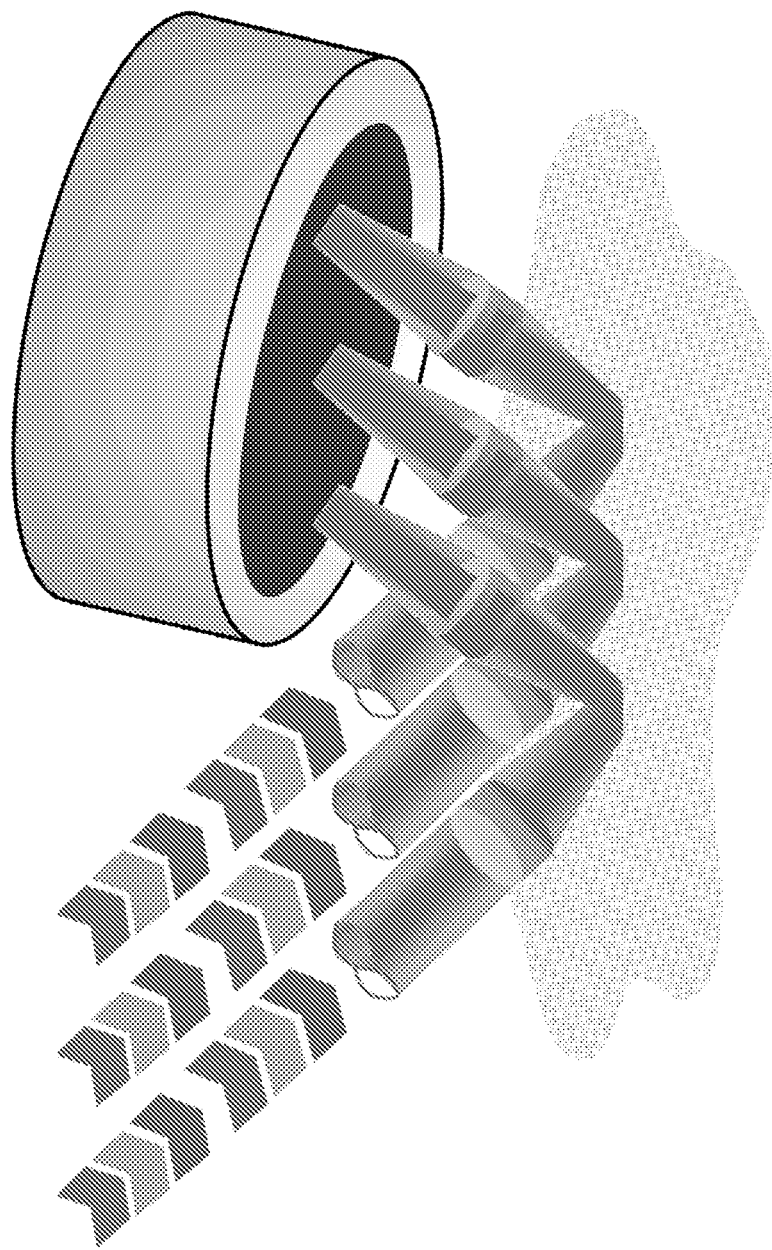
FIG. 12 illustrates using the pulsed beam in accordance with the present invention in a reflective approach to the specimen or media under test. Portrayed is a linear scan step pattern such that each illumination site is identical in illumination area leading to near-identical data capture at the detector.
Figure 13:
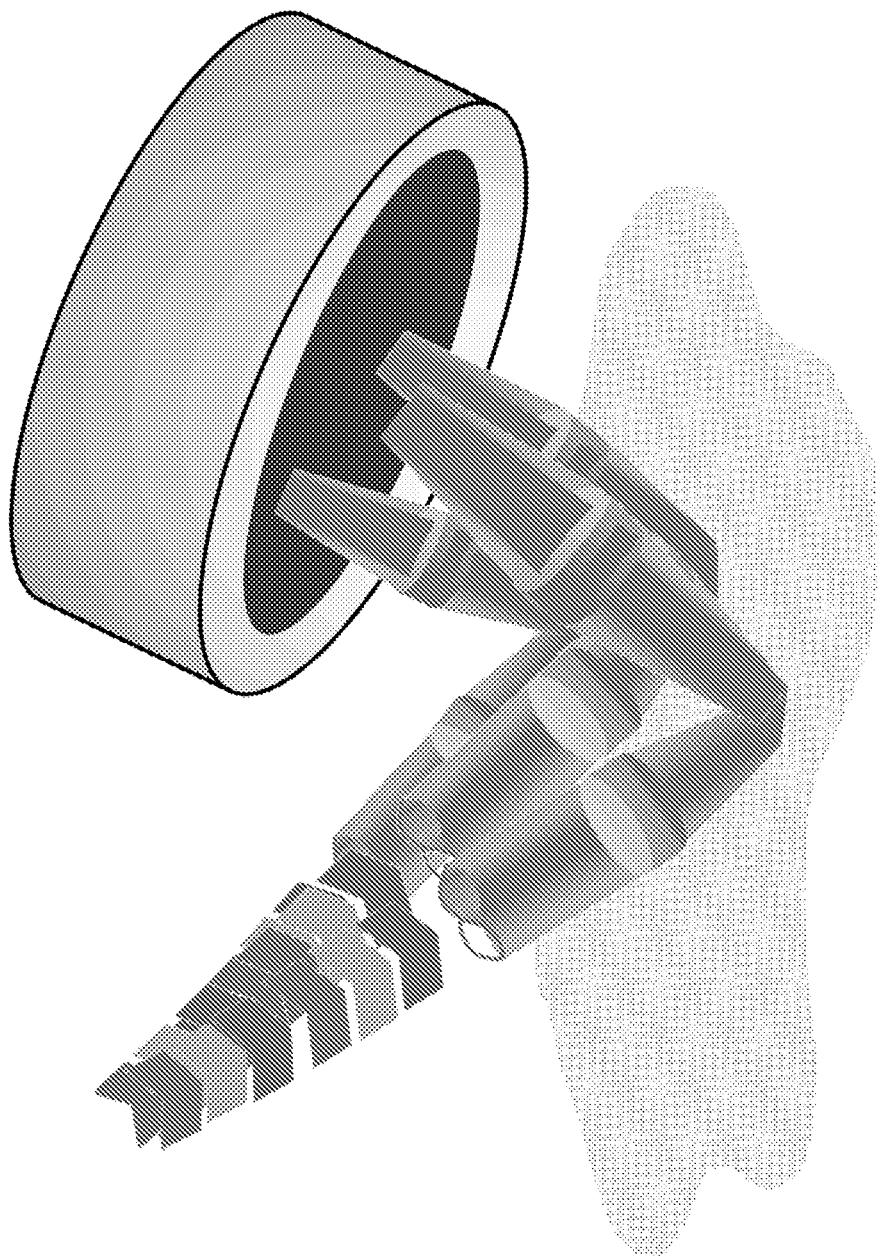
FIG. 13 is another proposed reflective scanning pattern where the illuminating beam is angled in order to gather data from two or more scan sites. The angled beams create slightly different scan site areas (such that the data collected at the detector must be adjusted to account for these variations.)

An important aspect of the inventive optical detection method is the application can be in both a transmissive approach as well as a reflective approach. Employing a reflective illumination data gathering method increases options for scanning configurations. With respect to the human body, transmission scanning is limited to certain accessible areas on the body such as the handweb, earlobe, nostril, cheek, eyelid, or fingers and toes, whereas reflective scanning expands typical locations on the human body to include the wrist, upper arm, abdomen, lower back, thigh, and calf as to where a sensor can be attached or worn for both spot and continuous monitoring. FIGS. 12 and 13 illustrate using the pulsed beam in a reflective approach to the specimen or media under test. Both linear scan steps as well as angular scan patterns can be exercised for reflective data collection. As noted, with linear scan stepping, each illumination site is identical in illumination area leading to near-identical data capture at the detector as in FIG. 12. Another proposed reflective scanning pattern where the illuminating beam is angled in order to gather data from two or more scan sites is portrayed in FIG. 13. The angled beams create slightly different scan site areas (such that the data collected at the detector must be adjusted to account for these variations.)

The following is a set of parameters of the scanning pattern and hardware for especially preferred embodiments of prior embodiments: Range of motion: 1-3 mm with step-and-settle times plan of <1 ms to <1 second (depending on data capture); Pattern of motion: linear or arc, linear precision <0.01 mm or angular precision of <1 mrad; System volume: small as possible; Actuation: piezo-linear or motor-rotary; Very low power, battery operated; Ability to return to set position and hold; Robustness for surviving temperature, shock, and humidity in field use; Embedded controller for ease of system integration.

Each "scan column" with the time-based narrow band spectroscopy sees a matrix of skin components. By moving the "scan column", data capture ensures a comprehensive inclusion of more skin conditions yielding better averaged values of glucose in interstitial fluid for each measurement "set."

One option of creating this emitter housing is with photo-definable glass-ceramics, machining of a metal or plastic, or by injection molding the housing.

Figure 2:
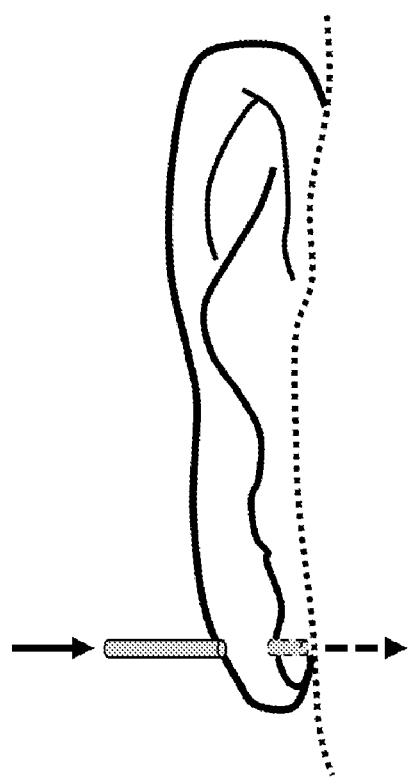
FIG. 2 is a side view which illustrates a pulsed beam as it passes through a liquid medium of an earlobe.
Figure 3:
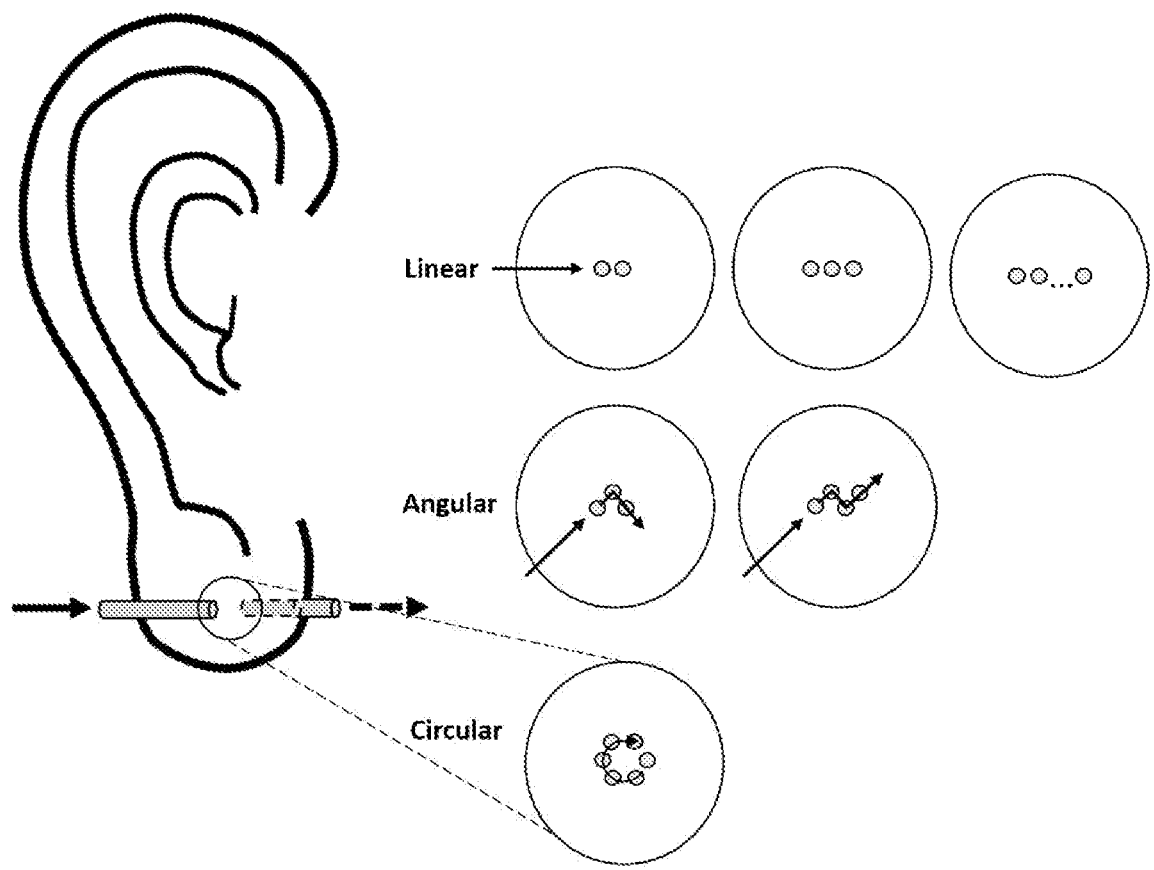
FIG. 3 is a front view of FIG. 2 and includes details of six different spot patterns for three options of multi-site scanning patterns: linear, non-linear, and circular.
Figure 4:
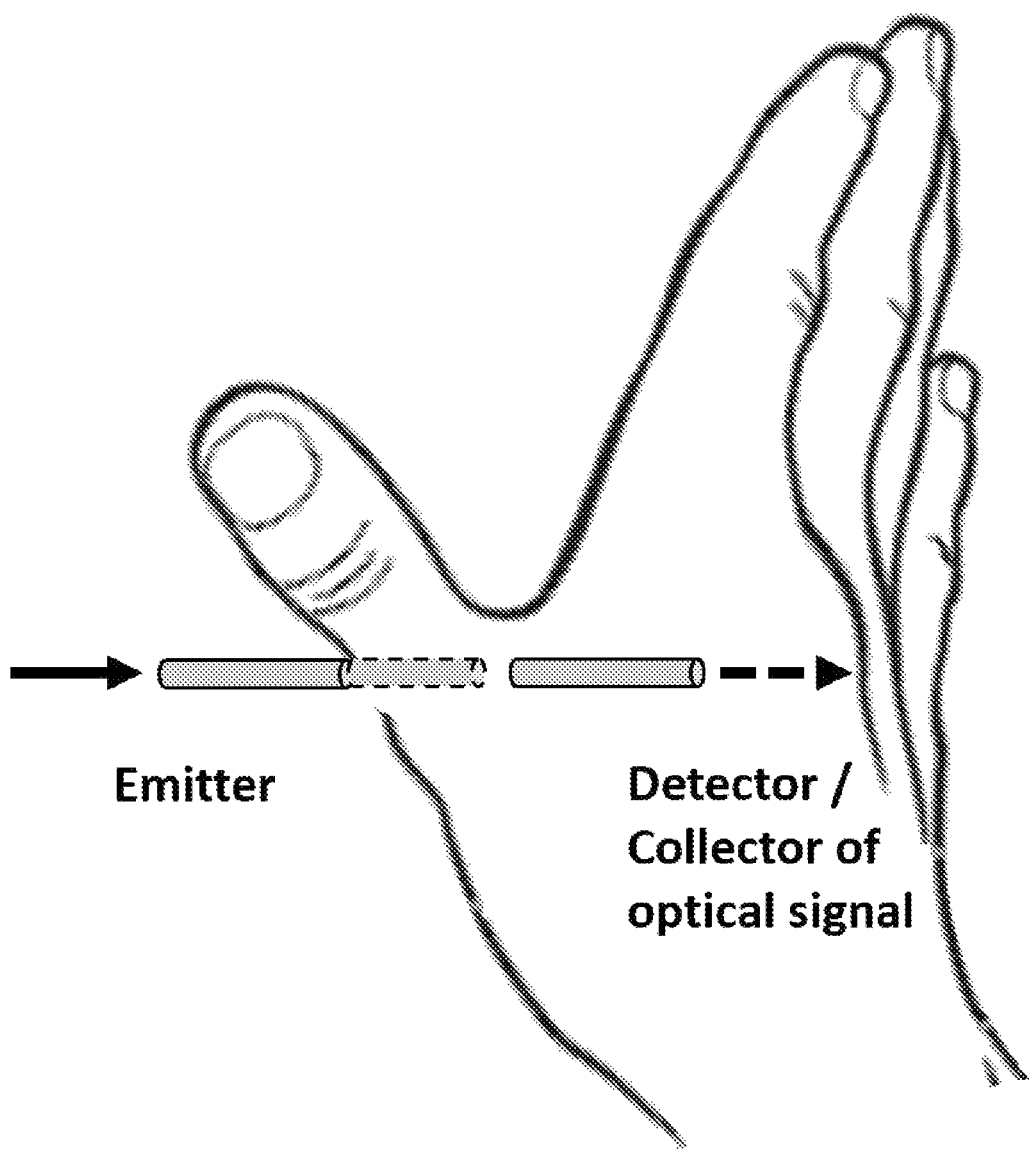
FIG. 4 illustrates a pulsed beam as it passes through a liquid medium of a hand web.
Figure 5:
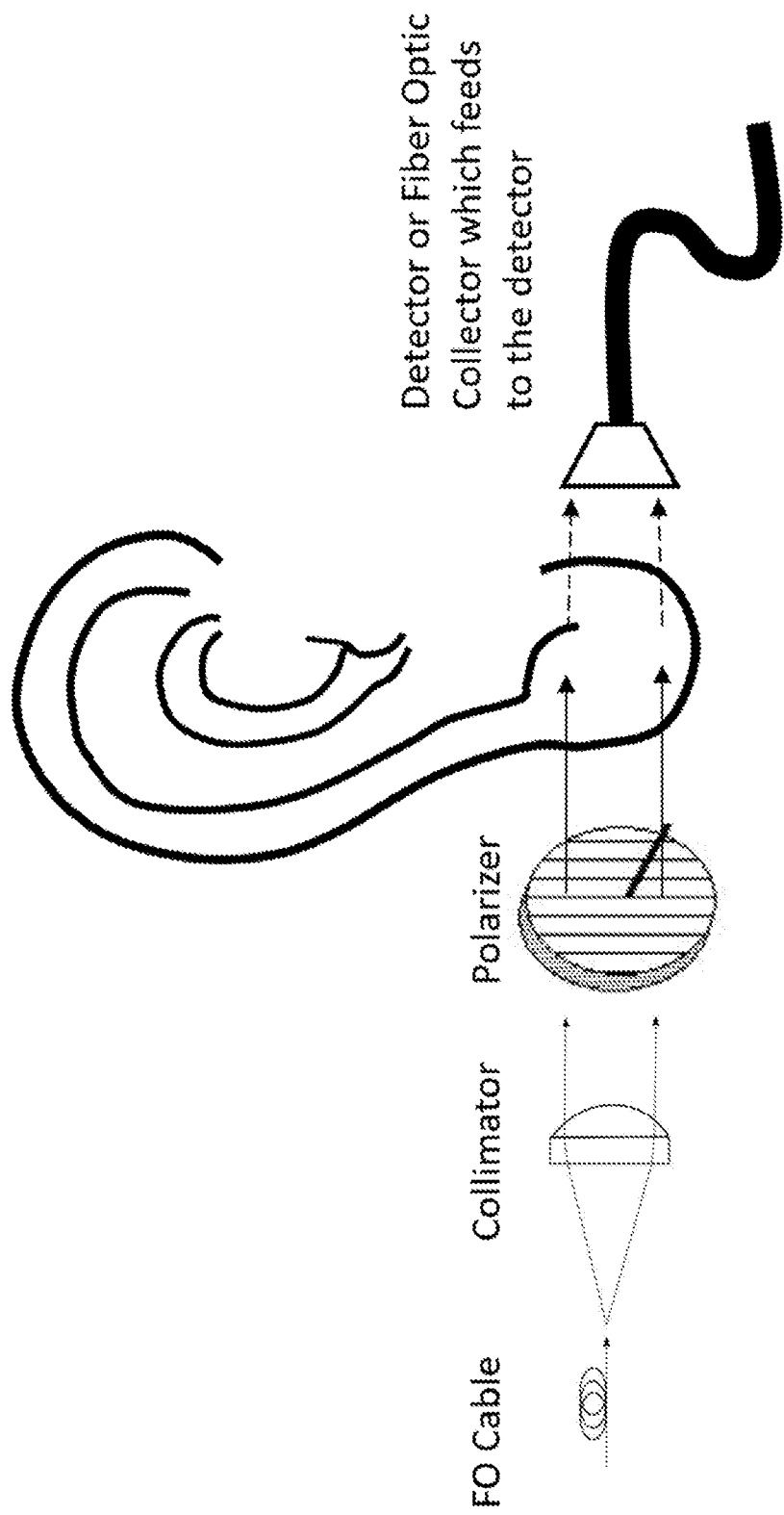
FIG. 5 illustrates a concept showing how polarized light is collected to feed a detector and incorporated into the present invention.

The inventive concepts already described herein can be applied to a wearable device using a reflection technique or be used in a device that can, in essence, be clipped on to a suitable portion of the human body, examples of which include a handweb or earlobe, which are illustrated in FIGS. 2 and 4, respectively. If a clip-on type device is desired, it may be beneficial to also use a fiber optic collector, or some other collection device, which serves to make the skin clamp device smaller and lighter, may enable increasing the sample collection area and may serve to concentrate the collected optical data allowing use of a smaller detector element. It might also be desirable to use polarized light because it may enhance absorption by glucose molecules and/or it may help to prevent absorption by other compounds in skin. Different types of light polarization might be implemented to achieve optimum absorption and minimized scattering, so linear and/or circular polarization might enhance overall accuracy, precision, and reliability of target species measurement.

This brings the reader to additional processes and apparatus disclosed in connection with the present invention. In implementing the inventive concepts already described, especially in a flowing liquid sampling matrix, it is desirable that the sensor system, which is comprised of electronic components, optical elements and software modules, minimize measurement error, which can come from several sources.

One potential source of measurement error is error caused by software modules (e.g., a software module which uses a faulty algorithm or does not execute it correctly).

Another source of measurement error is an accuracy limit of electronic components and optical elements used in the sensor system, and such error will always be present, and arise from multiple sources, a few illustrative examples of which are variations between detector elements and matched transimpedance amplifier performance. Errors caused by accuracy limits of electronic components and optical elements can be additive or subtractive of each other, all of which will lead to an accuracy limit for the sensor system. While the accuracy limit for a sensor system can be improved (or reduced) by a designer of the sensor system, it is possible to determine such a limit by exercising a calibration model based on a set of sample matrices with known analyte concentrations and the concept of such limit is stated in performance specifications for sensors.

Note that measurement error caused by accuracy limits is different from systemic error that may be introduced by a software module [e.g., rounding measurements/or another source.] Another source of measurement error is caused by motion of molecules passing in and out of the volume of the sample matrix. In a perfect theoretical world, movement of the liquid sampling matrix could be frozen, meaning there would be none; however, limits in electronic components and optical components, at least at the present time, prevent measurements from being taken in such a perfect theoretical state; instead, there will be some movement, and it can lead to error due to differing compositions of given molecules within the sample matrix over certain given times, especially if it is flowing. One way to address such potential error is to use a broader pulse beam. Another way to address such potential error, especially when the concentration of molecules of interest change over time (as is the case with glucose concentration in blood), is to minimize the time intervals of measurements while also greatly increasing sample size of measurements. This is the reason why it was previously disclosed that it was preferable to have a pulse frequency of at least 10 kHz or greater with a duty factor of at least 10%. In connection with the present disclosure, pulse frequency can also be increased by pulsing the signal source and the reference beam simultaneously (or near simultaneously) and also pulsing the interference source and the reference beam simultaneously (or near simultaneously), especially when two detectors are used, rather than one, to detect infrared radiation from the simultaneously (or near simultaneously) pulsed beams. With the addition of a second detector, additional error (of the accuracy limit type) can be added, but such error can be minimized when the two detectors are configured with an optically co-axial orientation. An example of an especially preferred embodiment of two detectors uses a silicon photodiode stacked on top of an indium gallium arsenide photodiode along a co-axial optical axis.

In an especially preferred embodiment of the present invention, the sample volume of the liquid sampling matrix is configured so that a sampling error within a given time period caused by changes of the targeted molecule passing in and out of the sample volume is approximately the same or less than a measurement error caused by an accuracy limit of the electronic components and the optical elements.

The present invention will now be described in even greater detail by reference to certain illustrative preferred embodiments.

Simultaneous or near simultaneous pulsing of respective pulse pairs (signal source & reference beam and interference source & reference beam) provides several benefits. First, the speed of sequential pulsing into a single detector is limited by the time for each pulse to achieve a suitable peak followed by a return of the detector to a near quiet state or essentially its noise floor. Second, with the ability to increase the frequency of the pulse rate of the pulse pairs, the system can measure samples that exhibit a fast change nature such as high-speed flow in a process pipe or batch reactor. Third, and possibly most importantly, a higher degree of noise cancellation may be achieved with the simultaneous pulse pairs "seeing" the exact same particle environment such that the Raleigh, Mie, and geometric scattering of each wavelength pulse energy will match to a higher degree. For purposes of the present invention, near simultaneous pulsing will have near unity but recognizes that efficiency of pulsing may mean some difference in pulsing due to efficiency and inherent limits, and anything within approximately 5% to 10% will be deemed near simultaneous pulsing.

Figure 14:
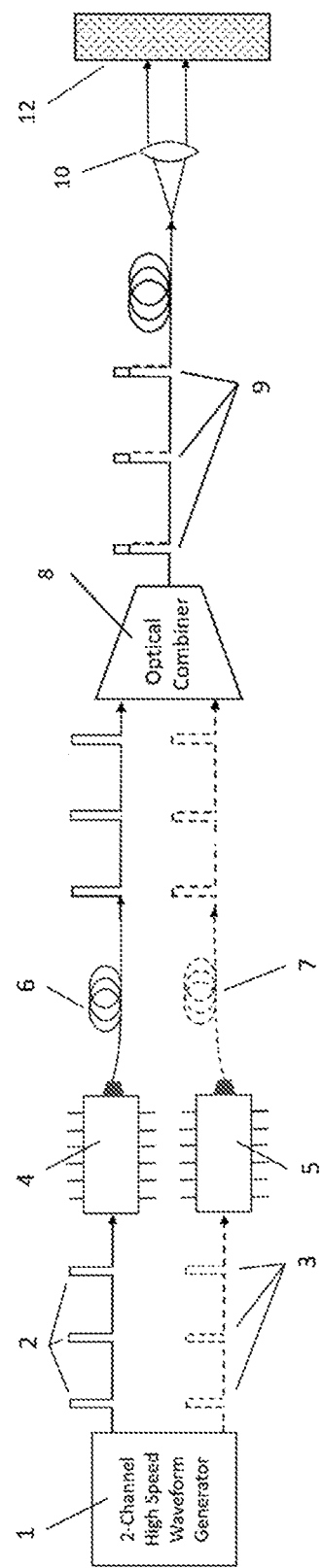
FIG. 14 illustrates an optical setup illustrating a pairing of two lasers driven simultaneously (or near simultaneously) according to the present invention.

FIG. 14 illustrates a simultaneous or near simultaneous pulsing pair which uses an optional collimator 10 and the pulsed paired beam can be used in a transmissive or reflective system (a transmissive system may be more suitable for measuring flowing liquids in, e.g., a pipe, whereas a reflective system may be more suitable for measuring flowing liquids inside of a reactor or a living body). If the liquid sampling matrix has interfering molecules, as is the case with measurement of glucose in a human body, at least one additional interference source can be added, and that at least one additional interference source can be paired with the reference beam. It bears note that the frequency of the pulsed pair of interference beam and reference beam need not be the same as that of the signal beam and reference beam, especially if the concentration of the interfering molecules in the liquid sampling matrix changes at a different rate than that of the target molecules, and it might allow for faster sampling using the signal beam and reference beam pairing if the frequency of the interference beam and reference beam pairing is less than that of the signal beam and reference beam pairing.

Simultaneous or near simultaneous pulsing can be achieved by implementing more than one detector through the use of a beam splitter system, detector stacking, or adjacent detectors with appropriate band pass filter optics such that each detector sees primarily only one of the wavelengths of the pulse pair employed.

Figure 15:
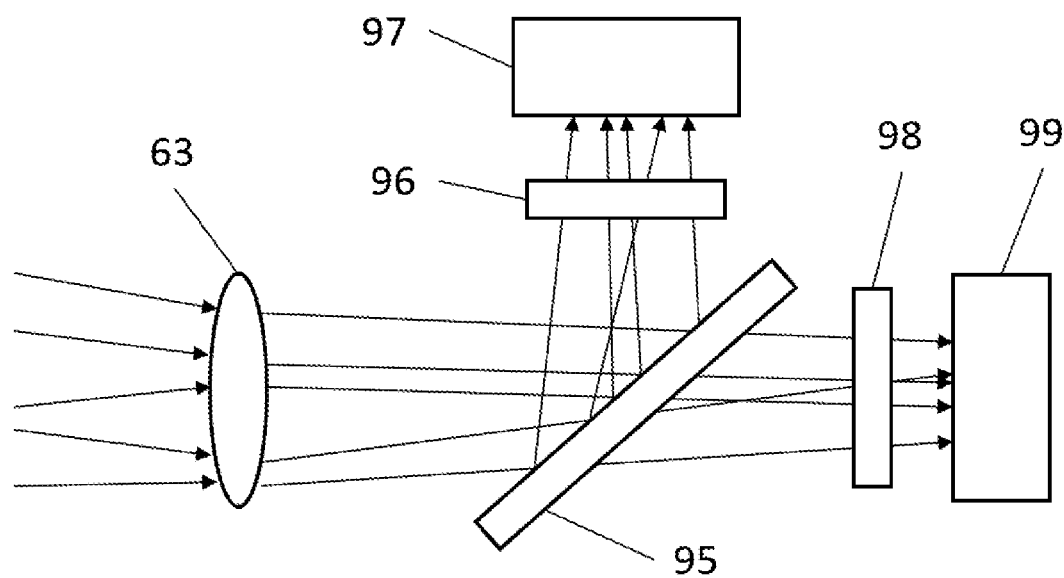
FIG. 15 illustrates a lens system (63) captures emitted light energy from the sample matrix and directs the light energy to an optical beam splitter (95). Depending on the design and configuration of the beam splitter, reflected light is sent towards a filter (96) which may or may not be used followed by a detector (97). Light passing through the optical beam splitter (95) is sent towards a filter (98) which may or may not be used followed by a detector (99).
Figure 16:
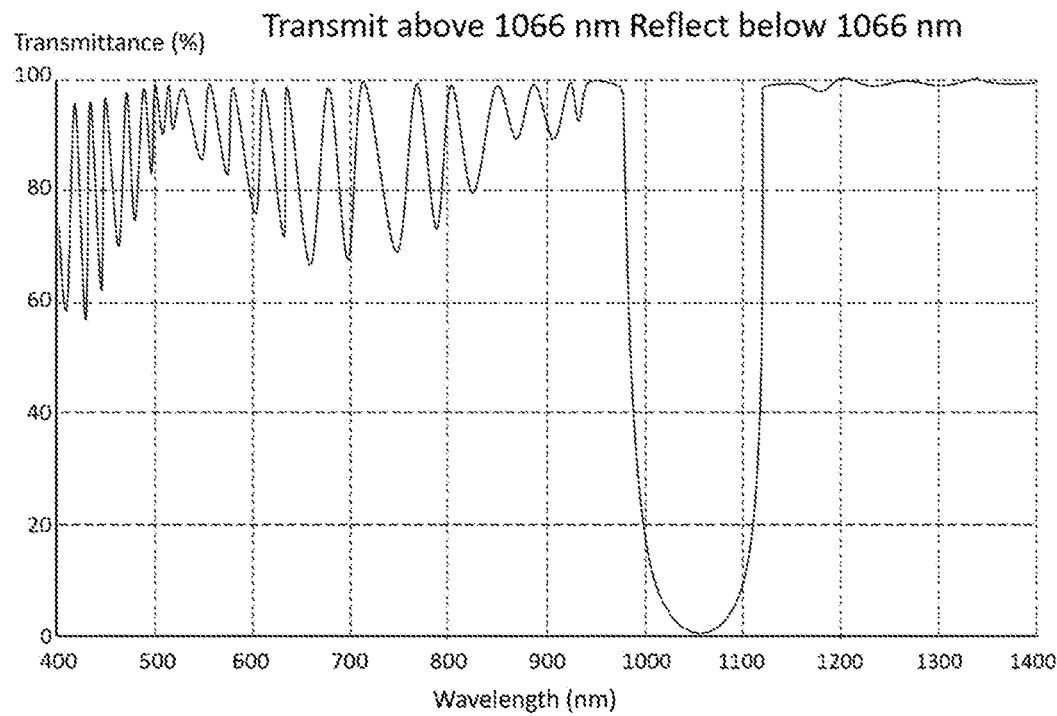
FIG. 16 provides an illustrative example of a transmittance plot of the optical beam splitter in FIG. 15 that will transmit light above 1066 nm and reflect light below 1066 nm while FIG. 17 provides an illustrative example of a transmittance plot of the optical beam splitter in FIG. 15 that will transmit light below 1066 nm and reflect light above 1066 nm.
Figure 17:
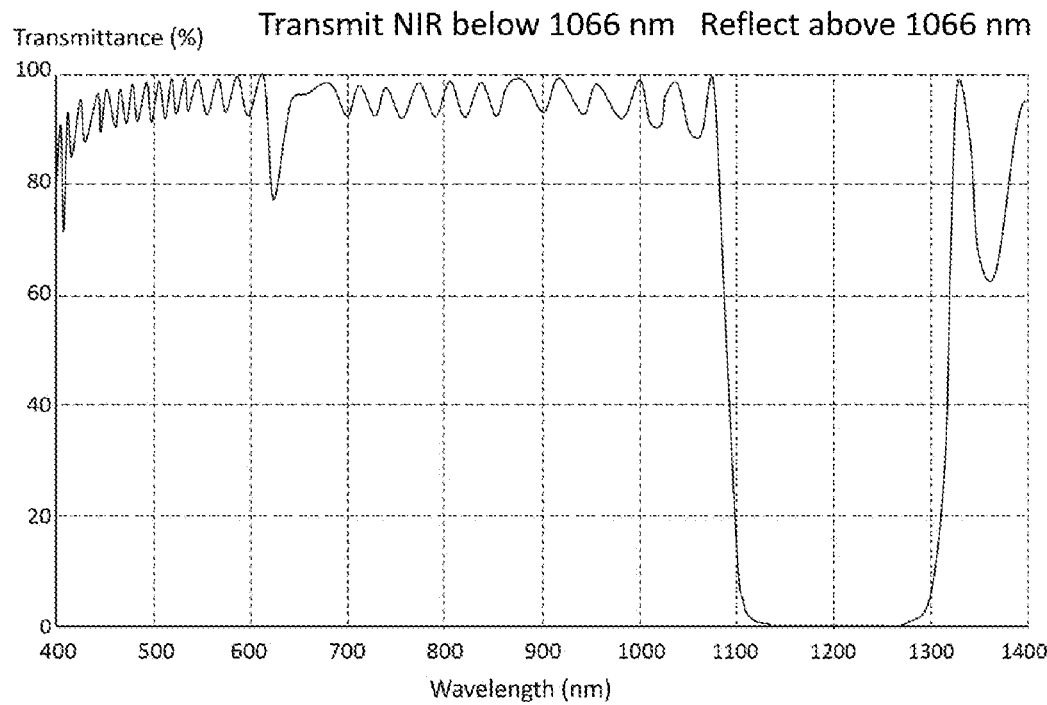
Figure 18:
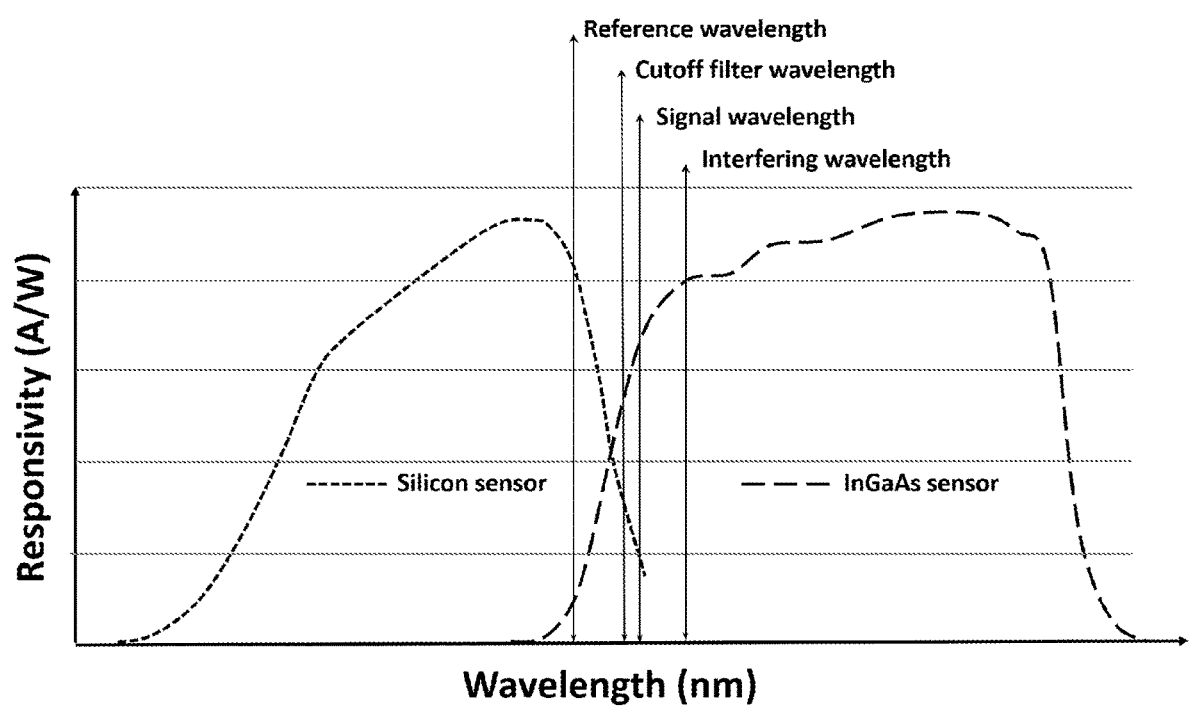
FIG. 18 illustrates a responsivity vs wavelength plot showing the performance of a typical silicon photodetector and an InGaAs photodetector. Overlaid are markers indicating a Reference wavelength that would be detected by the silicon photodetector, approximately where a cutoff filter wavelength might be directed, and two additional wavelengths, signal wavelength and interfering wavelength, that would be detected by the InGaAs photodetector. The specific sensitivity ranges of these two types of photodetectors enable configurations where the detector elements may be stacked or located adjacently within a single housing.
Figure 19:
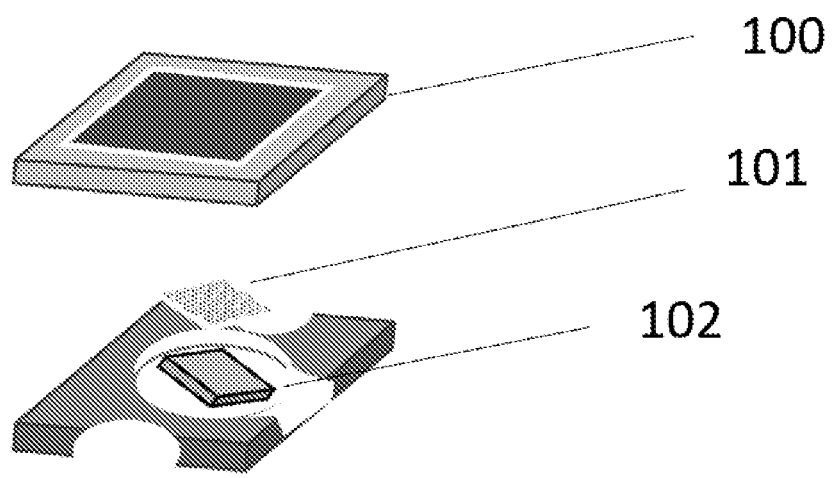
FIG. 19 illustrates a configuration where a silicon photodetector (100) may be located above a cutoff filter (101) that may or may not be employed and located above an InGaAs photodetector (102).
Figure 20:
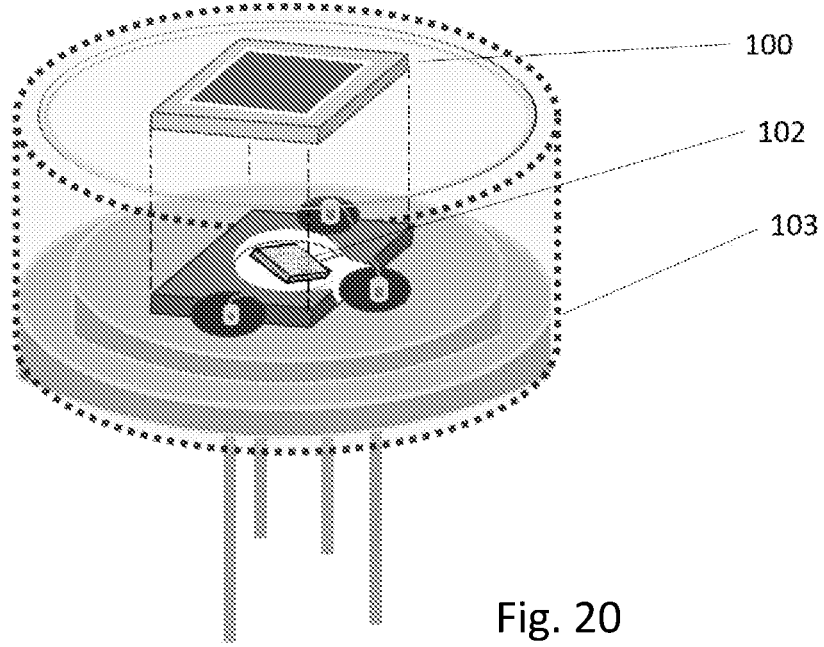
FIG. 20 illustrates how a stacked detector configuration can be installed into a typical TO hermetic can.
Figure 21:
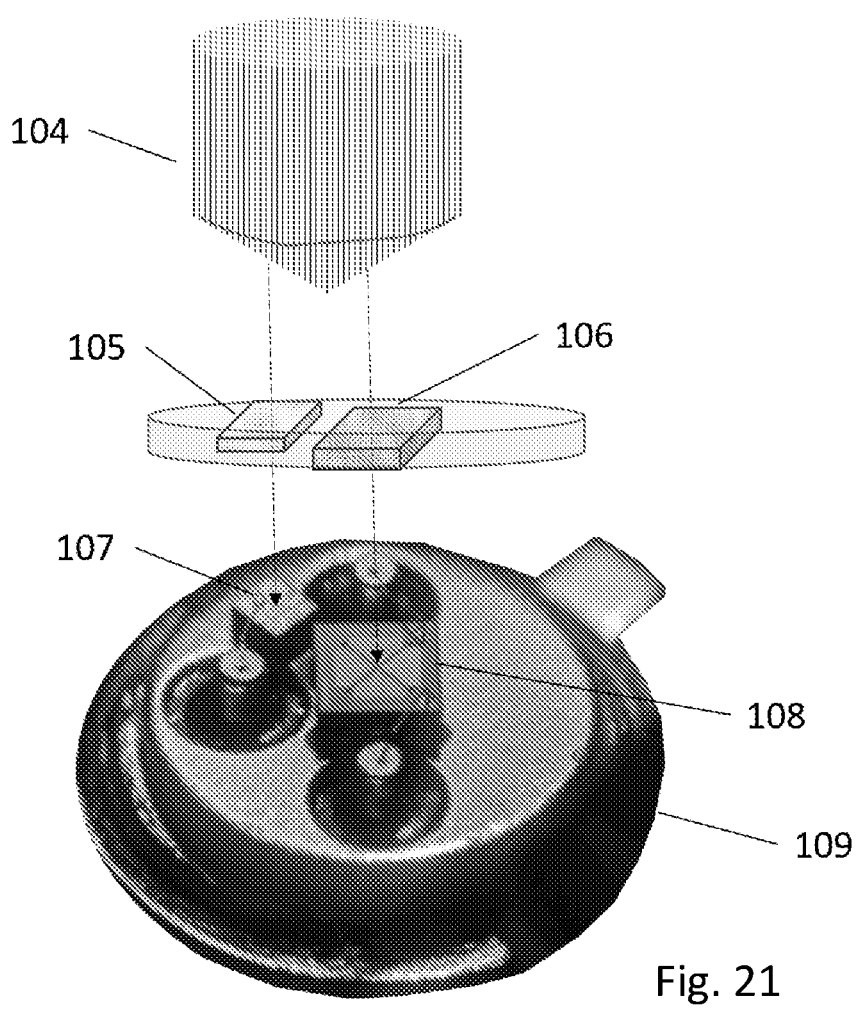
FIG. 21 illustrates how two types of detectors (107, 108) can be co-located adjacently in one detector housing. This detector configuration requires the use of either or both bandpass filters (105, 106) for their respective wavelengths of interest such that the filters are directly above the detectors. Of special note is that the emitted light energy beam (104) only partially interacts with each detector, whereas with a stacked detector or beam splitter configuration, the full beam impinges on the detectors.
Figure 22:
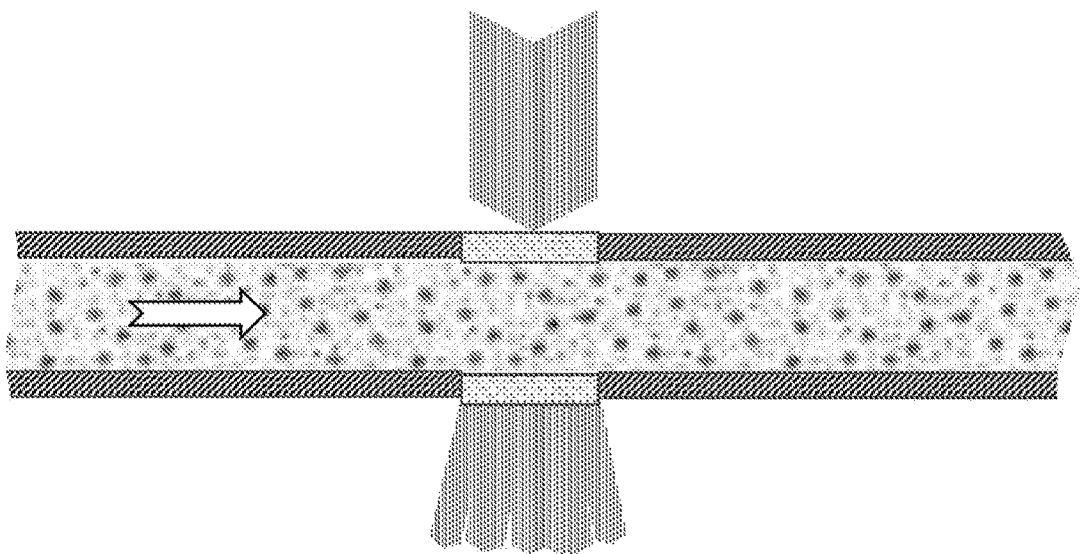
FIG. 22 illustrates a transmissive sensor system applied to a vessel where the sample matrix has a velocity component such as in a pipe.
Figure 23:
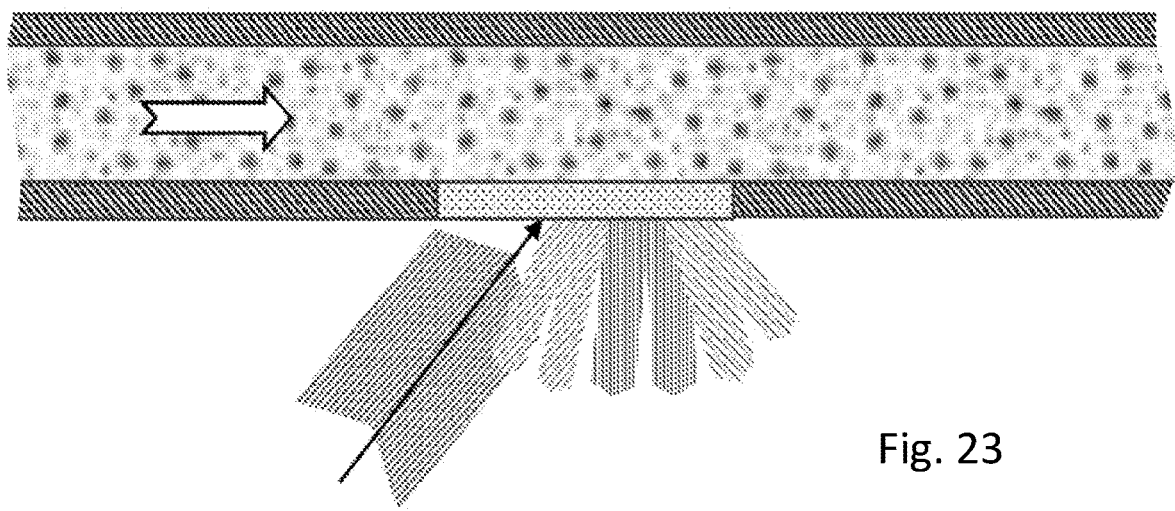
FIG. 23 illustrates a reflective sensor system applied to a vessel where the sample matrix has a velocity component such as in a batch reactor.

In a first illustrative example, which uses a dichroic beam splitter 95, light energy leaving the sample matrix is directed to one or more beam splitters. Based upon the nature and configuration of the beam splitter(s), the reference wavelength beam may pass directly to detector number one (99), or be reflected and directed to detector number two (97) as shown in FIG. 15. The other beam, being either the signal or interference wavelength, will experience the opposite effect and be directed to one or more other detector(s). In either case, the resulting optical output directed through a dichroic beam splitter or set of beam splitters provides elements of common emitted light energy from the sample matrix that reach each of two or more detectors simultaneously or there abouts timewise. FIG. 16 illustrates the case where beam splitter 95 transmits above 1066 nm to detector 99 and reflects below 1066 nm to detector 97 while FIG. 17 illustrates the case where beam splitter 95 transmits below 1066 nm to detector 99 and reflects above 1066 to detector 97.

It is worth noting that additional options include addition of further beam splitters to accommodate additional wavelength light sources for adapting to more target and/or interfering analytes.

A filter on one detector or more than one detector (shown as 96 and 98 in FIG. 15) can be employed for selection of a particular wavelength of light passing to each detector.

As with U.S. Pat. No. 9,606,053, "Reduction of Scattering Noise When Using NDIR with a Liquid Sample", a ratioing method will be applied to pulse pairs from the detectors such that a simultaneous reference and signal value can be compared for minimizing scattering noise present from a liquid medium enabling a more precise measurement of the spectral absorption of the signal wavelength by the target analyte(s).

Use of a beam splitter to separate laser pulses by wavelength requires two separate detectors which may add cost and increase size. By stacking two separate detectors that have specific sensitivities and optionally using a blocking filter on one of the detectors, the same result is achieved with a lower cost and smaller form factor. For the system to work for both sensing and calibration management, both the target and interfering analyte(s) wavelengths must be greater than the cutoff filter, if used, in front of the lower, second detector. Having both detector elements so closely co-located, they will experience less environmental condition differences than with two separately packaged detector elements, no matter how closely the separate detectors are mounted. The top detector, potentially constructed of silicon, will be responsive for the reference ($\lambda r$) wavelength and be transparent to longer wavelengths. A cutoff filter blocking the reference wavelength from reaching the bottom detector may be employed between the upper and lower detectors. The bottom detector, potentially constructed of InGaAs, will be responsive to the signal ($\lambda s$) and interference ($\lambda j$) wavelengths.

A third configuration of detectors may be employed with simultaneous pulsing where the detectors are both located in the same housing. This design employs multiple detectors co-located within a single housing but not stacked. Custom band pass filters are employed to select chosen wavelengths to reach their respective detector elements. One downside to this approach derives from the actual light received at each detector is only a portion of the total light delivered to the total potential sensing area of the detector housing. With stacked detectors or two+detectors with light directed to them through/by beam splitters, essentially the entire light "beam" is delivered to each detector with the same area and intensity relative to each wavelength.

With any multi-detector system, there will be performance variations between the two or more detectors. In comparison, this innovation highlights the art of the single detector system of U.S. Pat. No. 9,606,053 "Reduction of Scattering Noise When Using NDIR with a Liquid Sample" being so powerful by minimizing variables, and thereby improving system repeatability and reliability.

With multiple detectors configured with a beam splitter (s), with stacked detectors, or with adjacent detectors, performance of each splitter/filter/detector system can, and likely will, vary. These variations must be managed by a calibration system at the manufacturing stage.

Another consideration with adjacent detectors is that only a portion of the entire light "beam" impinges on each detector element, so orientation of the detector housing with respect to the impinging beam is another factor to consider in manufacturing and subsequent calibration.

There are benefits to the incorporation of polarization filters with a multi-detector system. Being able to polarize either or both the emitted signal ($\lambda s$) and interference ($\lambda j$) wavelengths will enable a refinement to the detection system should certain analytes have a chiral nature where spectral absorption of one chiral form will be greater or lesser, and this differentiation could would be isolated by the appropriately polarized filter and subsequently have an impact on the ultimate emitted beam energy reaching the respective detector.

While the invention described herein with reference to certain preferred embodiments, these embodiments have been presented by way of example only, and not to limit the scope of the invention. Additional embodiments thereof will be obvious to those skilled in the art having the benefit of this detailed description. Further modifications are also possible in alternative embodiments without departing from the inventive concept.

What is claimed is:

1. A process for quantifying a concentration of a targeted molecule in a liquid sample, comprising:
   pulsing a signal beam with a signal pulsed source;

pulsing a reference beam with a reference pulsed source;
spatially combining the pulsed signal beam and the pulsed reference beam into a single radiation beam which passes into the liquid sample;
detecting a pulsed signal beam output and a pulsed reference beam output after the single radiation beam passes out of the liquid sample;
processing the pulsed signal beam output and the pulsed reference beam output to obtain a value over a preselected period of time; and
calculating a concentration level of the targeted particle in the liquid sample based on the value;
wherein the signal pulsed source emits radiation at a signal bandwidth which is coincident with an absorption band of the targeted particle while the reference pulsed source emits radiation at a reference wavelength which is not coincident with the absorption band; and
wherein the signal pulsed source is separate from the reference pulsed source.

2. The process of claim 1 wherein the absorption band includes 1,150 nm.

3. The process of claim 2 wherein the reference wavelength is comprised of a second narrow bandwidth which includes 1,064 nm.

4. The process of claim 3 wherein the signal bandwidth is a first narrow bandwidth.

5. The process of claim 4 wherein the reference bandwidth is a second narrow bandwidth.

6. The process of claim 3 wherein the signal beam is pulsed at a frequency of 10 KHz or more.

7. The process of claim 1 wherein the signal beam is pulsed at a frequency of 10 KHz or more.

8. The process of claim 1 wherein a first particle environment in the liquid sample traversed by the signal beam is substantially identical to a second particle environment in the liquid sample traversed by the reference beam.

9. The process of claim 1 wherein the signal beam interrogates a signal beam sample volume which is substantially identical to a reference beam sample volume which is interrogated by the reference beam.

10. The process of claim 1 wherein the pulsed signal beam output is detected by a first detector and the pulsed reference beam output is detected by a second detector.

11. The process of claim 10 wherein the first detector and the second detector are configured with an optically co-axial configuration.

12. The process of claim 1 wherein the pulsed signal beam output and the pulsed reference beam output are detected by a single detector.

13. A process for quantifying a concentration of a targeted molecule in a liquid sample in which at least one interfering molecule coexists with the targeted molecule, comprising:
pulsing a signal beam with a signal pulsed source;
pulsing a reference beam with a reference pulsed source;
pulsing an interference beam with an interference pulsed source;
spatially combining the pulsed signal beam, the pulsed reference beam, and the pulsed interference beam into a single radiation beam which passes into the liquid sample;
detecting a pulsed signal beam output, a pulsed reference beam output, and a pulsed interference beam output after the single radiation beam passes out of the liquid sample;
processing the pulsed signal beam output and the pulsed reference beam output to obtain a first value over a first preselected period of time;
processing the pulsed interference beam output and the pulsed reference beam output to obtain a second value over a second preselected period of time;
using the second value to obtain a calibration curve adjustment representative of optical interference represented by the at least one interfering molecule concentration; and
calculating a concentration level of the targeted particle in the liquid sample based on the first value and the calibration curve adjustment;
wherein the signal pulsed source emits radiation at a signal bandwidth which is coincident with an absorption band of the targeted particle and the interference pulsed source emits radiation at an interference bandwidth which is coincident with a second absorption band of the at least one interfering molecule while the reference pulsed source emits radiation at a reference wavelength which is not coincident with the absorption band or the second absorption band.

14. The process of claim 13 wherein the signal bandwidth is a first narrow bandwidth, the interference bandwidth is a second narrow bandwidth and the reference wavelength is a third narrow bandwidth.

15. The process of claim 14 wherein the pulsed signal beam output and the pulsed interference beam output are detected by a first detector and the pulsed reference beam output is detected by a second detector.

16. The process of claim 15 wherein the first detector and the second detector are configured with an optically co-axial configuration.

17. The process of claim 15 wherein the first detector is adjacent to the second detector within a single housing.

* * * * *